United States Patent
Nishizawa et al.

(10) Patent No.: US 7,364,595 B2
(45) Date of Patent: Apr. 29, 2008

(54) COMPOSITION FOR HAIR BLEACHING OR HAIR DYEING

(75) Inventors: Eiichi Nishizawa, Tokyo (JP); Takashi Matsuo, Tokyo (JP); Hajime Miyabe, Tokyo (JP)

(73) Assignee: Kao Corporation, Tokyo (JP)

( * ) Notice: Subject to any disclaimer, the term of this patent is extended or adjusted under 35 U.S.C. 154(b) by 199 days.

(21) Appl. No.: 10/535,185

(22) PCT Filed: Nov. 27, 2003

(86) PCT No.: PCT/JP03/15153

§ 371 (c)(1), (2), (4) Date: May 17, 2005

(87) PCT Pub. No.: WO2004/050049

PCT Pub. Date: Jun. 17, 2004

(65) Prior Publication Data

US 2006/0123564 A1 Jun. 15, 2006

(30) Foreign Application Priority Data

Nov. 28, 2002 (JP) ............................. 2002-345585

(51) Int. Cl.
*A61K 7/13* (2006.01)
(52) U.S. Cl. .................. 8/405; 8/552; 8/554; 8/581; 8/619; 8/632
(58) Field of Classification Search ............ 8/405, 8/552, 554, 581, 619, 632, 101
See application file for complete search history.

(56) References Cited

U.S. PATENT DOCUMENTS 6,540,791 B1* 4/2003 Dias .................... 8/111
2004/0133996 A1 7/2004 Wolff et al.

FOREIGN PATENT DOCUMENTS

| GB | 2 188 948 | 10/1987 |
|----|-----------|---------|
| JP | 57-192310 | 11/1982 |
| JP | 63-051314 | 3/1988 |
| JP | 63-313717 | 12/1988 |
| JP | 04-059721 | 2/1992 |
| JP | 05-112423 | 5/1993 |
| JP | 09-059136 | 3/1997 |
| JP | 2003-081791 | 3/2003 |
| JP | 2003-146850 | 5/2003 |
| JP | 2004-67652 | 3/2004 |
| WO | WO 02/087515 | 11/2002 |

OTHER PUBLICATIONS

Shin-Etsu silicones, Catalogue of silicones for cosmetics, published by Shin-Etsu Chemical Co., Ltd. on Sep. 2001, pp. 1-4 (with partial English translation).
Shin-Etsu silicones, Catalogue of reactive-unreactived modified silicone oils, published by Shin-Etsu Chemical Co., Ltd. on Mar. 1997, pp. 1-3 (with partial English Translation).
Catalogue of silicones for personal care, published by Toray-Dow Corning-Silicone Corporation on Oct. 2000, pp. 1-4 (with partial English translation).

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Provided is a hair bleach or dye composition containing an amino-modified silicone, a highly polymerized silicone having a number-average degree of polymerization of 1000 or greater, a cationic polymer and an oxidizing agent.

The hair bleach or dye composition of the present invention does not give a discomfort upon washing or shampooing of the treated hair, can bleach or dye the hair uniformly from root to tip without damaging the hair by this treatment, add to the hair a good color and luster, and a good feel of the hair, manageability and hair retention after drying, and is also good in durability of these effects and stability.

13 Claims, No Drawings

COMPOSITION FOR HAIR BLEACHING OR HAIR DYEING

FIELD OF THE INVENTION

The present invention relates to an oxidative hair bleach or dye composition.

BACKGROUND OF THE INVENTION

Oxidative bleaching or dyeing agents which bleach or dye the hair by the oxidation reaction in the presence of an alkali agent or an oxidizing agent have been used popularly for bleaching or dyeing the hair.

Oxidative bleaching or dyeing agents however tend to damage the hair. For example, upon washing with water, shampooing or drying of the treated hair, the hair tangles, becomes hard or stiff, has a deteriorated color, loses luster or has poor manageability. Such hair damage is accumulated by the repetition of bleaching or dyeing and is particularly eminent in the tip of the hair which has been treated more frequently than the other portions of the hair.

In order to deal with such a problem, an additive having a conditioning action is added. For example, there are reports on the addition of a silicon derivative such as amino-modified silicone oil in order to dye the hair with a deep color tone (refer to JP-A-1982-192310), addition of an amino-containing polyorganosiloxane to give the hair with flexible touch and improve the hair setting property (refer to JP-A-1997-59136), and addition of a highly polymerized silicone or derivative thereof in order to prevent the hair damage and improve the feel of the hair (refer to JP-A-1988-313717 and JP-A-1992-59721).

In the bleaching or dyeing, the agent is washed away by water and a shampoo after the treatment and most of the additive having a conditioning action is inevitably lost from the hair. The amount of the agent remained on the hair is very small so that the addition does not bring about a satisfactory effect.

SUMMARY OF THE INVENTION

In the present invention, there is thus provided a hair bleach or dye composition containing an amino-modified silicone, a highly polymerized silicone having a number average molecular weight of 1000 or greater, a cationic polymer, an oxidizing agent and an alkali agent.

DETAILED DESCRIPTION OF THE INVENTION

The present invention relates to a hair bleach or dye composition which gives a pleasant feeling upon washing or shampooing of the treated hair, can bleach or dye the hair uniformly from root to tip without damaging the hair, gives the hair with good color and luster, and good hair feel, manageability and hair retention after drying, and is also good in durability of these effects and stability.

The present inventors have found that the above-described problems can be overcome by using an amino-modified silicone, a highly polymerized silicone and a cationic polymer in combination in a hair bleach or dye composition.

[Amino-Modified Silicone]

As the amino-modified silicone, any one of those having an amino or ammonium group can be used. Either amino-modified silicone oils having all or some of the terminal hydroxyl groups blocked with a methyl group or the like, or terminal-unblocked amodimethicones may be used. For example, amino-modified silicones represented by the below-described formula (1) are preferred. They contribute to uniform bleaching or dyeing of the hair, remain well on the hair to give it with various effects such as softness and smoothness upon wetting, and a vivid and deep color, luster, softness, smoothness, volume (body), manageability and moisture retention upon drying, and enables the prolongation of these effects.

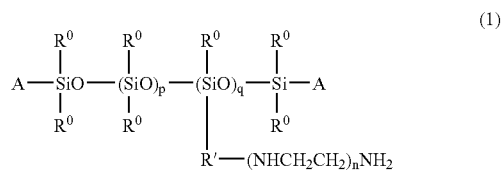

(wherein, $R^0$ represents a hydroxyl group, a hydrogen atom or R, R represents a substituted or unsubstituted monovalent hydrocarbon group having from 1 to 20 carbon atoms, A represents R, a group $—R'—(NHCH_2CH_2)_n NH_2$, a group OR or a hydroxyl group, R' represents a divalent hydrocarbon group having from 1 to 8 carbon atoms, n stands for 0 to 3, and p and q are numbers, the sum of which is, in number average, 10 or greater but less than 1000, preferably 30 or greater but less than 1000, more preferably 40 or greater but less than 800. The amino equivalent is 200 g/mol to 30000 g/mol, preferably 400 g/mol to 10000 g/mol, more preferably 600 g/mol to 5000 g/mol).

Specific examples of the commercially available amino-modified silicone include amino-modified silicone oils such as "SF8451C" (product of Dow Corning Toray Silicone, viscosity: 600 mm²/s, amino equivalent: 1700 g/mol), "SF8452C" (product of Dow Corning Toray Silicone, viscosity: 700 mm²/s, amino equivalent: 6400 g/mol), "SF8457C" (product of Dow Corning Toray Silicone, viscosity: 1200 mm²/s, amino equivalent: 1800 g/mol), "KF8003" (trade name; product of GE Toshiba Silicones, viscosity: 1850 mm²/s, amino equivalent: 2000 g/mol), and "KF867" (trade name; product of GE Toshiba Silicones, viscosity: 1300 mm²/s, amino equivalent: 1700 g/mol); and amodimethicone emulsions such as "SM8704C" (product of Dow Corning Toray Silicone, amino equivalent: 1800 g/mol). The amino-modified silicone oil may be incorporated in the emulsion form. The emulsion of the amino-modified silicone can be prepared by mechanical emulsification (high-shear mechanical mixing of the amino-modified silicone and water) or chemical emulsification (emulsification of the amino-modified silicon with water and an emulsifying agent), or combination of them; or by emulsion polymerization.

The amino-modified silicone content in the whole composition is preferably from 0.01 to 30 wt. %, more preferably from 0.05 to 20 wt. %, still more preferably from 0.1 to 10 wt. %. The term "the whole composition" as used herein means a mixture of a first part containing an alkali agent and a second part containing an oxidizing agent such as hydrogen peroxide just before use when the hair bleach or dye composition of the present invention is a two-part type, while it means a mixture of these two parts with a third part just before use when the composition is a three-part type.

[Highly Polymerized Silicone]

Examples of the highly polymerized silicone having a number-average degree of polymerization of 1000 or greater include dimethylpolysiloxane (INCI name: dimethicone), methylphenylpolysiloxane, hydroxy terminated dimethylpolysiloxane (INCI name: dimethiconol) and slightly crosslinked silicone rubbers as described in WO96/31188. These silicones contribute to uniform bleaching or dyeing of the hair and rinsability of the resulting composition; remain well on the hair to add various effects to the hair such as softness, smoothness and good finger combing property upon wetting, and a vivid and deep color, luster, softness, smoothness, volume (body), manageability and moisture retention upon drying; and enable the prolongation of these effects.

The highly polymerized silicone has a number-average degree of polymerization of 1000 or greater, preferably 1500 or greater, more preferably 2000 or greater but less than 20000. Within this range of the degree of polymerization, partially substituted silicones such as fluorine-modified silicones, alcohol-modified silicones, polyether-modified silicones, epoxy-modified silicones, alkyl-modified silicones and amino-modified silicones can also be used. The content of the highly polymerized silicone in the whole composition is preferably from 0.01 to 30 wt. %, more preferably from 0.05 to 20 wt. %, still more preferably from 0.1 to 10 wt. %.

Specific examples of the commercially available highly polymerized silicone having a number-average degree of polymerization of 1000 or greater include "SH200-1,000,000 Cs (product of Dow Corning Toray Silicone), "TSF451-100MA" (product of GE Toshiba Silicones), "BY11-026" (product of Dow Corning Toray Silicone, a solution of a highly polymerized silicone diluted with a low-viscosity silicone), "KF9008" (product of Shin-etsu Silicone, a solution of a highly polymerized silicone diluted with a cyclic silicone), "BY22-050A" (product of Dow Corning Toray Silicone, a cationic emulsion of a highly polymerized silicone), "BY22-060" (product of Dow Corning Toray Silicone, a cationic emulsion of a solution obtained by diluting a highly polymerized silicone with a low viscosity silicone), "BY22-020" (product of Dow Corning Toray Silicone, a cationic emulsion of a solution obtained by diluting a highly polymerized silicone with liquid paraffin), and "KM904" (product of Shin-etsu Silicone, a cationic emulsion of a solution obtained by diluting a highly polymerized silicone with a low viscosity silicone).

In addition, silicones other than the amino-modified silicones and highly polymerized silicones (for example, dimethylpolysiloxane having a degree of polymerization less than 1000, cyclic polysiloxanes, phenylpolysiloxanes, and modified silicones other than the amino-modified silicones) can be incorporated.

The total content of the amino-modified silicone, highly polymerized silicone and other silicones in the whole composition is preferably from 0.02 to 40 wt. %, more preferably from 0.1 to 20 wt. %, still more preferably from 0.2 to 15 wt. % from the standpoints of sufficient effects and inhibition of stickiness. These silicones are incorporated at a content ratio so that a reduced amino equivalent expressed by the below-described equation falls within a range of preferably from 500 to 100000 g/mol, more preferably from 1000 to 80000 g/mol, still more preferably from 2000 to 50000 g/mol.

Reduced amino equivalent (g/mol)={total weight of all the silicones in 1 g of the whole composition (g/g)}/{total moles of amino, imino and ammonium groups of the amino-modified silicone in 1 g of the whole composition (mol/g)}

In the above-described equation, "total weight of all the silicones in 1 g of the whole composition (g/g)", and "total moles of amino, imino and ammonium groups of the amino-modified silicone in 1 g of the whole composition (mol/g)" are determined in the following manner.

Silicones are fractionated from each of the first part and second part (and third part when the composition is a three-part type) and the total weight of all the silicones (g) and total moles of the amino, imino and ammonium groups of the amino-modified silicone (mol) are determined. Based on the mixing ratio of the parts in the whole composition, the total weight of all the silicones in 1 g of the whole composition (g/g) and total moles of the amino, imino and ammonium groups of the amino-modified silicone in 1 g of the whole composition (mol/g) are calculated. In accordance with the above-described equation to calculate a reduced amino equivalent, the reduced amino equivalent (g/mol) is determined.

[Cationic Polymer]

Either one or both of the first and second parts of the hair bleach or dye composition of the present invention contain a cationic polymer. The cationic polymer contributes to uniform bleaching or dyeing of the hair and good rinsability of the resulting composition, remains well on the hair to add various effects to the hair such as softness, smoothness and good finger combing property upon wetting, and a vivid and deep color, luster, softness, smoothness, volume (body), manageability and moisture retention upon drying, and at the same time, enables the prolongation of these effects. In particular, it adds to the hair softness, smoothness, good finger combing property and good rinsability upon shampooing.

The term "cationic polymer" means a polymer having a cationic group or a group which can be ionized into a cationic group. Examples of the cationic polymer include aqueous solutions of a polymer having, on the side chain of its polymer chain, an amino or ammonium group, or a diallyl quaternay ammonium salt as a constituent such as cationic cellulose derivatives, cationic starches, cationic guar gum derivatives, polymers or copolymers of a diallyl quaternary ammonium salt, and quaternized polyvinylpyrrolidone derivatives. Of these cationic polymers, polymers containing a diallyl quaternary ammonium salt as a constitutional unit, quaternized polyvinylpyrrolildone derivatives, and cationic cellulose derivatives are preferred from the viewpoints of the above-described effects and stability of the composition, of which the polymers or copolymers of a diallyl quaternary ammonium salt and cationic cellulose derivatives are more preferred and the polymers or copolymers of a diallyl quaternary ammonium salt are still more preferred.

The diallyl quaternary ammonium salts having a skeleton represented by the below-described formula (2) or (3) are preferred.

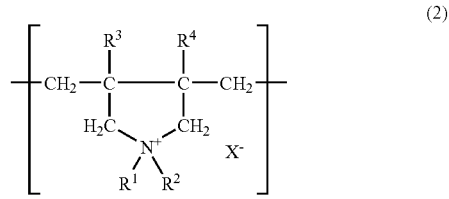

-continued

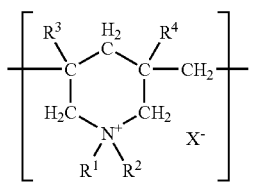

(3)

(wherein, $R^1$ and $R^2$ may be the same or different and each independently represents a hydrogen atom, or an alkyl group, aryl group (such as phenyl group), hydroxyalkyl group, amidoalkyl group, cyanoalkyl group, alkoxyalkyl group or carboalkoxyalkyl group having from 1 to 18 carbon atoms, $R^3$ and $R^4$ may be the same or different and each independently represents a hydrogen atom, an alkyl group having from 1 to 3 carbon atoms, or a phenyl group, and $X^-$ represents an anion (chloride ion, bromide ion, iodide ion, sulfate anion, sulfonate anion, methylsulfate anion, phosphate anion, nitrate anion or the like)).

Examples of the monomer constituting a copolymer with a diallyl quaternary ammonium salt include acrylic acid and methacrylic acid and salts thereof, and acrylamide. Of these, acrylic acid and methacrylic acid, and salts thereof are preferred.

Specific examples of the polymer or copolymer of a diallyl quaternary ammonium salt include dimethyldiallylammonium chloride polymer, dimethyldiallylammonium chloride/acrylic acid copolymer and dimethyldiallylammonium chloride/acrylamide copolymer. Examples of the commercially available products of them include "Merquat 100", "Merquat 280", "Merquat 295" and "Merquat 550" (each, product of Calgon), of which "Merquat 280" and "Merquat 295" are preferred.

As the quaternized polyvinylpyrrolidone derivative, those represented by the following formula (4) are preferred.

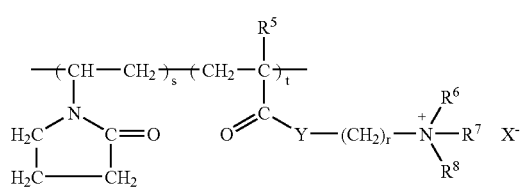

(4)

(wherein, $R^5$ represents a hydrogen atom or an alkyl group having from 1 to 3 carbon atoms, $R^6$, $R^7$ and $R^8$ may be the same or different, and each independently represents a hydrogen atom or an alkyl group, hydroxyalkyl group, amidoalkyl group, cyanoalkyl group, alkoxyalkyl group or carboalkoxyalkyl group having from 1 to 4 carbon atoms, Y represents an oxygen atom or an imino group, r stands for an integer of from 1 to 10, s and t stand for numbers, the sum of which is from 20 to 8,000, and $X^-$ has the same meaning as described above).

The quaternized polyvinylpyrrolidone derivative to be used in the present invention has preferably a molecular weight of from 10000 to 2000000, more preferably from 50000 to 1500000. Examples of the commercially available product include "Gafquat 734", "Gafquat 755" and "Gafquat 755N" (each, product of ISP, JAPAN).

As the cationic cellulose derivatives, those represented by the following formula (5) are preferred.

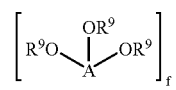

(5)

(wherein, A represents a residue of an anhydroglucose unit, f stands for an integer of from 50 to 20000, and each of $R^9$ represents a substituent represented by the following formula (6)).

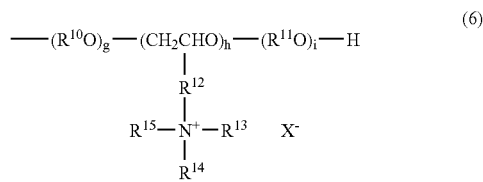

(6)

(wherein, $R^{10}$ and $R^{11}$ each represents an alkylene group having from 2 or 3 carbon atoms, g stands for an integer from 0 to 10, h stands for an integer from 0 to 3, i stands for an integer from 0 to 10, $R^{12}$ represents an alkylene or hydroxyalkylene group having from 1 to 3 carbon atoms, and $R^{13}$, $R^{14}$ and $R^{15}$ may be the same or different, and each independently represents an alkyl group, aryl group or aralkyl group having carbon atoms up to 10, or may form a heterocycle containing the nitrogen atom in this formula, and $X^-$ has the same meaning as described above).

The degree of cation substitution of such cationized cellulose derivatives, that is, the mean value of h per anhydroglucose unit preferably ranges from 0.01 to 1, more preferably from 0.02 to 0.5. The sum of g+i is 1 to 3 on average. The degree of cation substitution less than 0.01 is not sufficient. On the other hand, it may exceed 1 but the degree of cation substitution not greater than 1 is preferred from the standpoint of a reaction yield. The cationic cellulose derivative to be used here has preferably a molecular weight of from 100000 to 3000000. Examples of the commercially available products include "Leogard G" and "Leogard GP" (each, product of Lion Co.), and "Polymer JR-125", "Polymer JR-400", "Polymer JR-30M", "Polymer LR-400" and "Polymer LR-30M" (each, product of Union Carbide Co.). Examples of the other cationic cellulose derivatives include hydroxyethyl cellulose dimethyldiallylammonium chloride, while examples of their commercially available products include "Celquat H-100" and "Celquat L-200" (each, product of National Starch and Chemical Co.).

Two or more of these cationic polymers may be used in combination. Their content in the whole composition is preferably from 0.001 to 20 wt. %, more preferably from 0.01 to 10 wt. %, still more preferably from 0.05 to 5 wt. %.

[Oxidizing Agent]

Examples of the oxidizing agent include hydrogen peroxide, urea peroxide serving as a hydrogen peroxide generator, melamine peroxide, sodium perborate, potassium perborate, sodium percarbonate and potassium percarbonate. Of these, hydrogen peroxide is preferred. The content of the oxidizing agent in the whole composition is preferably from 0.1 to 12 wt. %, more preferably from 0.5 to 9 wt. %, still more preferably from 1 to 6 wt. % from the standpoints of sufficient bleaching or dyeing effect, and reduction in hair damage and scalp irritation.

[Alkali Agent]

The hair bleach or dye composition of the present invention contains an alkali agent. Examples of the alkali agent include ammonia and salts thereof; alkanolamines such as monoethanolamine, isopropanolamine, 2-amino-2-methylpropanol and 2-aminobutanol, and salts thereof; alkanediamines such as 1,3-propanediamine and salts thereof; and carbonate salts such as guanidine carbonate, sodium carbonate, potassium carbonate, sodium bicarbonate and potassium bicarbonate. Of these, ammonia and monoethanolamine are preferred as the alkali agent, with combined use of ammonia or monoethanolamine with the carbonate salt being more preferred. Two or more of these alkali agents may be used in combination. Their content in the whole composition is preferably from 0.05 to 15 wt. %, more preferably from 0.1 to 10 wt. %, still more preferably from 0.2 to 5 wt. % from the standpoints of sufficient bleaching or dyeing effect, and reduction in the hair damage and scalp irritation.

Of the above-described alkali agents, ammonia and alkanolamines, and salts thereof are preferred. As the ammonium salt, ammonium carbonate and ammonium bicarbonate are preferred. As the alkanolamine and salts thereof, monoethanolamine and salts thereof are preferred. Addition of them while adjusting their content to fall within the below-described range is more preferred.

The sum of the content (a) of ammonia and salts thereof in terms of ammonia and the content (b) of monoethanolamine and salts thereof in terms of monoethanolamine is preferably from 0.05 to 15 wt. %, more preferably from 0.1 to 10 wt. %, still more preferably from 0.2 to 5 wt. % in the whole composition, from the standpoints of sufficient bleaching or dyeing effect, and reduction in hair damage, scalp irritation and nasal irritation. The ratio (a)/(b) is preferably 0.01:1-2.0:1, more preferably, 0.02:1-1:1, even more preferably, 0.05:1-0.5:1.

[Intermediate for Oxidation Dye]

When the hair bleach or dye composition of the present invention is a hair bleach composition, it does not contain a dye, and when it is a hair dye composition, it contains, in the first part thereof, an intermediate for oxidation dye.

As the intermediate for oxidation dye, known precursors and couplers ordinarily employed for hair dyes can be used. Examples of the precursor include para-phenylenediamine, toluene-2,5-diamine, 2-chloro-para-phenylenediamine, N-methoxyethyl-paraphenylenediamine, N,N-bis(2-hydroxyethyl)-paraphenylenediamine, 2-(2-hydroxyethyl)-paraphenylenediamine, 2,6-dimethyl-paraphenylenediamine, 4,4'-diaminodiphenylamine, 1,3-bis(N-(2-hydroxyethyl)-N-(4-aminophenyl)amino)-2-propanol, PEG-3,3,2'-paraphenylenediamine, paraaminophenol, paramethylaminophenol, 3-methyl-4-aminophenol, 2-aminomethyl-4-aminophenol, 2-(2-hydroxyethylaminomethyl)-4-aminophenol, orthoaminophenol, 2-amino-5-methylphenol, 2-amino-6-methylphenol, 2-amino-5-acetamidophenol, 3,4-diaminobenzoic acid, 5-aminosalicylic acid, 2,4,5,6-tetraminopyrimidine, 2,5,6-triamino-4-hydroxypyrimidine, 4,5-diamino-1-(4'-chlorobenzyl)pyrazole and 4,5-diamino-1-hydroxyethylpyrazole, and salts thereof.

Examples of the coupler include metaphenylenediamine, 2,4-diaminophenoxyethanol, 2-amino-4-(2-hydroxyethylamino)anisole, 2,4-diamino-5-methylphenetole, 2,4-diamino-5-(2-hydroxyethoxy)toluene, 2,4-dimethoxy-1,3-diaminobenzene, 2,6-bis(2-hydroxyethylamino)toluene, 2,4-diamino-5-fluorotoluene and 1,3-bis(2,4-diaminophenoxy)propane, metaaminophenol, 2-methyl-5-aminophenol, 2-methyl-5-(2-hydroxyethylamino)phenol, 2,4-dichloro-3-aminophenol, 2-chloro-3-amino-6-methylphenol, 2-methyl-4-chloro-5-aminophenol, N-cyclopentyl-metaaminophenol, 2-methyl-4-methoxy-5-(2-hydroxyethylamino)phenol, 2-methyl-4-fluoro-5-aminophenol, resorcin, 2-methylresorcin, 4-chlororesorcin, 1-naphthol, 1,5-dihydroxynaphthalene, 1,7-dihydroxynaphthalene, 2,7-dihydroxynaphthalene, 2-isopropyl-5-methylphenol, 4-hydroxyindole, 5-hydroxyindole, 6-hydroxyindole, 7-hydroxyindole, 6-hydroxybenzomorpholine, 3,4-methylenedioxyphenol, 2-bromo-4,5-methylenedioxyphenol, 3,4-methylenedioxyaniline, 1-(2-hydroxyethyl)amino-3,4-methylenedioxybenzene, 2,6-dihydroxy-3,4-dimethylpyridine, 2,6-dimethoxy-3,5-diaminopyridine, 2,3-diamino-6-methoxypyridine, 2-methylamino-3-amino-6-methoxypyridine, 2-amino-3-hydroxypyridine and 2,6-diaminopyridine, and salts thereof.

Two or more of these precursors or couplers may be used in combination. The content of each of them in the whole composition is preferably from 0.01 to 5 wt. %, more preferably from 0.1 to 4 wt. %.

[Higher Alcohol]

The hair bleach or dye composition of the present invention preferably contains a higher alcohol from the standpoints of improvement in the feel of the hair and stability. The higher alcohol is effective not only for forming a structure with a surfactant to prevent separation but also for improving the feel of the hair upon rinsing.

As the higher alcohol, those having from 8 to 22 carbon atoms are preferred, with those having from 16 to 22 carbon atoms being more preferred. Specific examples include cetyl alcohol, stearyl alcohol and behenyl alcohol, and mixtures thereof. Among them, behenyl alcohol is preferred in consideration of its effect on feel of the hair.

Two or more of these higher alcohols may be used in combination. Their content in the whole composition is preferably from 0.01 to 20 wt. %, more preferably from 0.1 to 10 wt. %.

[Surfactant]

The hair bleach or dye composition of the present invention preferably contains a surfactant in order to emulsify the silicone or higher alcohol. As the surfactant, nonionic surfactants such as alkoxylated (for example, ethoxylated or propoxylated) higher alcohols having a linear or branched $C_{12-22}$ alkyl group, more specifically, polyoxyethylene (2-40) alkyl ethers can be used in an amount of from 1 to 40 wt. %, preferably from 2 to 20 wt. % in the whole composition from the viewpoint of stability. In consideration of the feel of the hair, combined use of a cationic surfactant such as mono (long-chain alkyl)trimethylammonium salt is preferred. As the mono(long-chain alkyl)trimethylammonium salt usable here, behenyltrimethylammonium chloride is preferred from the standpoints of feel of the hair and emulsifying performance. They are used preferably at a weight ratio of (cationic surfactant)/(nonionic surfactant+cationic surfactant) preferably not greater than 0.8, more preferably not greater than 0.6, still more preferably not greater than 0.4. Use of an anionic surfactant is not recommended because it sometimes damages the feel of the hair.

When the surfactant and higher alcohol are added at a weight ratio of from 10:1 to 1:10, preferably from 4:1 to 1:8, more preferably from 1:1 to 1:4, the first part and second part before mixing can be obtained in the cream form.

[Medium]

As a medium of the hair bleach or dye composition of the present invention, water and, if necessary, an organic solvent are used. Examples of the organic solvent include lower alkanols such as ethanol and 2-propanol, aromatic alcohols such as benzyl alcohol and benzyloxyethanol, polyols such as polypropylene glycol, 1,3-butanediol, diethylene glycol and glycerin, cellosolves such as ethyl cellosolve, butyl cellosolve and benzyl cellosolve, and carbitols such as ethyl carbitol and butyl carbitol.

[Form of Composition]

The hair bleach or dye composition of the present invention is, similar to oxidation type hair bleaches or hair dyes popularly used now, provided as a two-part composition composed of a first part containing an alkali agent and a second part containing an oxidizing agent such as hydrogen peroxide. To achieve better bleaching performances, it can be provided as a three-part composition composed of, in addition to the above-described two parts, a third part containing a powdery oxidizing agent made of a granulated persulfate (ammonium persulfate, potassium persulfate, sodium persulfate or the like). The first part and the second part can be prepared, for example, in the form of liquid, emulsion, cream, gel, paste or mousse. They can also be provided as an aerosol form. When the first part and the second part (and the third part when the composition is a three-part type) are mixed, the resulting mixture desirably has a viscosity such that it does not cause dripping when applied to the hair. The viscosity as measured by a Brookfield rotation viscometer ("B8R Viscometer", product of TOKIMEC) equipped with a helical stand is preferably from 2000 to 100000 mm$^2$/s. The viscosity is a value after 1 minute rotation using a "Rotor T-C" at 10 rpm.

With regards to the pH (25° C.) of the hair bleach or dye composition of the present invention, the first part and the second part preferably have a pH of from 8 to 12 and from 2 to 5, respectively. The pH of the composition upon use (upon mixing) is preferably from 7.5 to 12, more preferably from 8 to 11 from the standpoints of hair bleaching or dyeing effect and skin irritation. Examples of a pH regulator include, in addition to the above-described alkali agent, inorganic acids such as hydrochloric acid and phosphoric acid, organic acids such as citric acid, glycolic acid and lactic acid, hydrochlorides such as ammonium chloride and monoethanolamine hydrochloride, and phosphates such as monopotassium dihydrogen phosphate and disodium monohydrogen phosphate.

[Other Optional Components]

In addition to the above-described components, other components commonly employed as cosmetic raw materials can be added to the hair bleach or dye composition of the present invention. Examples of such optional components include direct dyes (acid dyes, basic dyes, disperse dyes, reactive dyes and the like), hydrocarbons, animal or plant oils or fats, higher fatty acids, penetration promoters, natural or synthetic high molecules, ethers, protein derivatives, hydrolysate proteins, amino acids, antiseptics, chelating agents, stabilizers, antioxidants, plant extracts, crude drug extracts, vitamins, colorants, perfumes and ultraviolet absorbers.

[Bleaching or Dyeing Method]

The hair bleaching or dyeing with the hair bleach or dye composition of the present invention may be performed, for example, by mixing the first part and the second part (and the third part when the composition is a three-part type) of the composition of the present invention, applying the mixture to the hair at from 15 to 45° C., allowing it to stand for from 1 to 60 minutes, preferably from 3 to 45 minutes for the composition to act on the hair, washing the hair and then drying the hair. In this case, removal of the hair bleach or dye composition with water by light wash, shampooing of the hair with a shampoo containing an anionic surfactant and subsequent washing with water allow the cationic polymer to be moderately washed away and the silicone to moderately remain on the hair, which ultimately allow good conditioning effects to appear. As the shampoo, an ordinary water-base shampoo containing about 5 to 20 wt. % of an anionic surfactant such as sodium lauryl ethoxy (1 to 3) sulfate is suited.

[Effects]

The amino-modified silicone contributes to the uniform hair bleaching or dyeing as described above, and it remains well on the hair so that it can add to the hair various effects such as softness and smoothness upon wetting, and a vivid and deep color, luster, softness, smoothness, volume (body), manageability and moisture retention upon drying, and enables the prolongation of these effects; however, it is insufficient in smooth finger combing property when wet and rinsability of the resulting composition. The present inventors have overcome these drawbacks by the use of a highly polymerized silicone in combination with the amino-modified silicone and moreover, have improved the above-described effects of the amino-modified silicone. Even by this measure, the composition is still insufficient in softness, smoothness, good finger combing property, and rinsability of the composition upon shampooing. The present inventors have succeeded in improving these properties and at the same time, improving the effects brought about by the amino-modified silicone and highly polymerized silicone by using a cationic polymer in combination.

EXAMPLES

In a manner known per se in the art, the first part components shown in Tables 1 and 2, the second part components shown in Tables 3 and 4, and the third part components shown in Table 5 were prepared.

TABLE 1

| | Fist part (in the cream form) (wt. %) | | | | | | | | | | |
| --- | --- | --- | --- | --- | --- | --- | --- | --- | --- | --- | --- |
| Pharmaceutical component | 1st part A | 1st part B | 1st part C | 1st part D | 1st part E | 1st part F | 1st part G | 1st part H | 1st part I | 1st part J | 1st part K |
| Amino-modified silicone (amino equivalent: 1800 g/mol, number-average degree of polymerization: 300) | 1.0*6 | 1.0 | 1.0 | 1.0 | 1.0 | 1.0 | 1.0 | 1.0 | 1.0*8 | — | 1.0*9 |

TABLE 1-continued

| Pharmaceutical component | First part (in the cream form) (wt. %) | | | | | | | | | | |
|---|---|---|---|---|---|---|---|---|---|---|---|
| | 1st part A | 1st part B | 1st part C | 1st part D | 1st part E | 1st part F | 1st part G | 1st part H | 1st part I | 1st part J | 1st part K |
| Amodimethicone (amino equivalent: 1800 g/mol, number-average degree of polymerization: 300, 40 wt. % emulsion) | — | 1.0 | — | — | — | — | 1.0 | 1.0 | — | — | — |
| Amino-modified highly polymerized silicone (amino equivalent: 20000 g/mol, number-average degree of of polymerization: 2000) | — | — | — | — | 5.0 | 5.0 | — | — | — | — | — |
| Highly polymerized methylpolysiloxane (number-average degree of polymerization: 2700) | — | — | — | 5.0 | — | — | — | — | — | — | — |
| Highly polymerized methylpolysiloxane (number-average degree of polymerization: 3800) | 1.5*6 | 1.5*7 | 1.5 | — | — | — | 1.5 | 1.5 | 1.5*8 | — | 1.5*9 |
| Methylpolysiloxane (number-average degree of polymerization: 550) | 4.0*6 | 4.0*7 | 4.0 | — | — | 0.5 | 4.0 | 4.0 | 4.0*8 | — | 4.0*9 |
| Dimethyldiallylammonium chloride.acrylic acid copolymer solution *1 | 2.0 | 2.0 | — | 2.0 | 2.0 | 2.0 | — | — | — | — | 2.0 |
| Dimethyldiallylammonium chloride polymer solution *2 | — | — | 1.0 | — | — | — | — | — | — | — | — |
| Dimethyldiallylammonium chloride.acrylamide copolymer solution *3 | 2.0 | 2.0 | — | — | — | — | — | — | — | — | 2.0 |
| Poly(dimethylmethylenepiperidinium chloride solution *4 | — | — | — | — | — | — | 0.2 | — | — | — | — |
| Cationic cellulose derivative *5 | — | — | — | — | — | — | — | 0.2 | — | — | — |
| Toluene-2,5-diamine solution (20 wt. %) | 1.0 | 1.0 | 1.0 | 1.0 | 1.0 | 1.0 | 1.0 | 1.0 | 1.0 | 1.0 | — |
| Resorcin | 0.4 | 0.4 | 0.4 | 0.4 | 0.4 | 0.4 | 0.4 | 0.4 | 0.4 | 0.4 | — |
| m-Aminophenol | 0.2 | 0.2 | 0.2 | 0.2 | 0.2 | 0.2 | 0.2 | 0.2 | 0.2 | 0.2 | — |
| Tetrasodium edetate dihydrate | 0.2 | 0.2 | 0.2 | 0.2 | 0 2 | 0.2 | 0.2 | 0.2 | 0.2 | 0.2 | 0.2 |
| Anhydrous sodium sulfite | 0.5 | 0.5 | 0.5 | 0.5 | 0.5 | 0.5 | 0.5 | 0.5 | 0.5 | 0.5 | 0.5 |
| Ascorbic acid | 0.5 | 0.5 | 0.5 | 0.5 | 0.5 | 0.5 | 0.5 | 0.5 | 0.5 | 0.5 | 0.5 |
| Propylene glycol | 6.0 | 6.0 | 6.0 | 6.0 | 6.0 | 6.0 | 6.0 | 6.0 | 6.0 | 6.0 | 6.0 |
| Cetanol | 7.0 | 7.0 | 7.0 | 7.0 | 7.0 | 7.0 | 7.0 | 7.0 | 7.0 | 7.0 | 7.0 |
| Polyoxyethylene (40) cetyl ether | 2.0 | 2.0 | 2.0 | 2.0 | 2.0 | 2.0 | 2.0 | 2.0 | 2.0 | 2.0 | 2.0 |
| Polyoxyethylene (2) cetyl ether | 1.0 | 1.0 | 1.0 | 1.0 | 1.0 | 1.0 | 1.0 | 1.0 | 1.0 | 1.0 | 1.0 |
| Stearyltrimethylammonium chloride solution (28 wt. %) | 3.0 | 3.0 | 3.0 | 3.0 | 3.0 | 3.0 | 3.0 | 3.0 | 3.0 | 3.0 | 3.0 |
| Octyldodecanol | 1.0 | 1.0 | 1.0 | 1.0 | 1.0 | 1.0 | 1.0 | 1.0 | 1.0 | 1.0 | 1.0 |
| Liquid paraffin | 1.0 | 1.0 | 1.0 | 1.0 | 1.0 | 1.0 | 1.0 | 1.0 | 1.0 | 1.0 | 1.0 |
| Strong aqueous ammonia (28 wt. %) | 1.0 | 1.0 | 1.0 | 1.0 | 1.0 | 1.0 | 1.0 | 1.0 | 1.0 | 1.0 | 1.0 |
| Ethanolamine | 3.5 | 3.5 | 3.5 | 3.5 | 3.5 | 3.5 | 3.5 | 3.5 | 3.5 | 3.5 | 3.5 |
| Ammonium hydrogen carbonate | 0.3 | 0.3 | 0.3 | 0.3 | 0.3 | 0.3 | 0.3 | 0.3 | 0.3 | 0.3 | 0.3 |
| Perfume | q.s. | q.s. | q.s. | q.s. | q.s. | q.s. | q.s. | q.s. | q.s. | q.s. | |
| Water | Balance | Balance | Balance | Balance | Balance | Balance | Balance | Balance | Balance | Balance | Balance |

*1 "Merquat 280" (a 40 wt. % aqueous solution, product of Calgon)
*2 "Merquat 100" (a 40 wt. % aqueous solution, product of Calgon)
*3 "Merquat 550" (a 8.5 wt. % aqueous solution, product of Calgon)
*4 "Gafquat 734" (product of ISP Japan)
*5 "Polymer JR-125" (product of Union Carbide)
*6 to 9 added after mixing.

TABLE 2

| First part (in the liquid form) Pharmaceutical component | (wt. %) Fist part L | First part M |
|---|---|---|
| Toluene-2,5-diamine solution (20 wt. %) | 1.0 | — |
| Resorcin | 0.4 | — |
| m-Aminophenol | 0.2 | — |
| Anhydrous sodium sulfite | 0.4 | 0.4 |
| Ascorbic acid | 0.4 | 0.4 |
| 2-Benzyloxyethanol | 18.0 | 18.0 |
| Ethanol | 3.0 | 3.0 |
| Polyoxyethylene (20) octyldodecyl ether | 16.0 | 16.0 |
| Polyoxyethylene (9) oleyl ether | 8.0 | 8.0 |
| Polyoxyethylene (3) tridecyl ether | 14.0 | 14.0 |
| Isostearyl glyceryl ether | 1.5 | 1.5 |
| Isostearyl pentaerythryl glyceryl ether | 4.0 | 4.0 |
| Stearyltrimethylammonium chloride solution (28 wt. %) | 7.0 | 7.0 |
| Oleyl alcohol | 3.0 | 3.0 |
| Ethanolamine | 6.0 | 6.0 |
| Perfume | q.s. | q.s. |
| Purified water | Balance | Balance |

TABLE 3

| Second part (in the cream form)<br>Pharmaceutical component | 2nd part A | 2nd Part B | 2nd Part C (wt. %) |
|---|---|---|---|
| Amino-modified silicone (amino equivalent: 1800 g/mol, number-average degree of polymerization: 300) | — | — | 1.0*3 |
| Amodimethicone (amino equivalent: 1800 g/mol, number-average degree of polymerization: 300, 40 wt. % emulsion) | — | 2.0 | — |
| Highly polymenzed methylpolysiloxane (number-average degree of polymerization: 2700) | — | 5.0 | — |
| Highly polymerized methylpolysiloxane (number-average degree of polymerization: 3800) | — | — | 1.5*3 |
| Methylpolysiloxane (number-average degree of polymerization: 550) | — | — | 4.0*3 |
| Dimethyldiallylammonium chloride.acrylic acid copolymer solution*1 | — | — | 2.0 |
| Dimethyldiallylammonium chloride polymer solution*2 | — | — | 1.0 |
| Aqueous hydrogen peroxide (35 wt. %) | 16.0 | 16.0 | 16.0 |
| 8-Quinolinol sulfate | 0.04 | 0.04 | 0.04 |
| Polyoxyethylene (40) cetyl ether | 1.0 | 1.0 | 1.0 |
| Polyoxyethylene (2) cetyl ether | 1.0 | 1.0 | 1.0 |
| Cetanol | 3.5 | 3.5 | 3.5 |
| 75 wt. % Phosphoric acid | Adjusted to pH 3 | Adjusted to pH 3 | Adjusted to pH 3 |
| Purified water | Balance | Balance | Balance |

*1"Merquat 280" (a 40 wt. % aqueous solution, product of Calgon)
*2"Merquat 100" (a 40 wt. % aqueous solution, product of Calgon)
*3added after mixing.

TABLE 4

| Second part (in the liquid form)<br>Pharmaceutical component | 2nd part D | 2nd Part E | 2nd Part F | 2nd part G (wt. %) |
|---|---|---|---|---|
| Aqueous hydrogen peroxide (35 wt. %) | 16.0 | 16.0 | 16.0 | 16.0 |
| 8-Quinolinol sulfate | 0.04 | 0.04 | 0.04 | 0.04 |
| Amodimethicone (amino equivalent: 1800 g/mol, number-average degree of polymerization: 300, 40 wt. % emulsion) | 2.0 | 2.0 | — | — |
| Highly polymerized dimethylsilicone emulsion (number-average degree of polymerization: 2700) | 6.0 | 6.0 | — | — |
| Dimethyldiallylammonium chloride.acrylic acid copolymer solution *1 | 1.0 | 2.0 | 2.0 | — |
| Dimethyldiallylammonium chloride polymer solution *2 | — | 2.0 | 2.0 | — |
| Stearyltrimethylammonium chloride solufion (63%) | 3.0 | 3.0 | 3.0 | 3.0 |
| Cetanol | 2.0 | 2.0 | 2.0 | 2.0 |
| Glycerin | 1.0 | 1.0 | 1.0 | 1.0 |
| 75 wt. % Phosphoric acid | Adjusted to pH 3 | Adjusted to pH 3 | Adjusted to pH 3 | Adjusted to pH 3 |
| Purified water | Balance | Balance | Balance | Balance |

*1 "Merquat 280" (a 40 wt. % aqueous solution, product of Calgon)
*2 "Merquat 100" (a 40 wt. % aqueous solution, product of Calgon)

TABLE 5

| Third part (in the granulated form)<br>Pharmaceutical component | 3rd part A (wt. %) |
|---|---|
| Sodium persulfate | 10.0 |
| Potassium persulfate | 16.0 |
| Ammonium persulfate | 26.0 |
| Anhydrous sodium metasilicate | 20.0 |
| Sodium silicate | 17.8 |
| Silicic acid anhydride | 1.0 |
| Sodium stearate | 5.0 |
| Sodium lauryl sulfate | 1.0 |
| Anhydrous tetrasodium edetate | 1.0 |
| β-Cyclodextrin | 0.2 |
| Xanthan gum | 1.0 |
| Sodium carboxymethylcellulose | 1.0 |

According to the combination and weight ratio as shown in Table 6, the first part, second part and third part are mixed. The resulting mixture is applied to the hair at a composition-hair ratio (by weight)=1:1. After the hair is allowed to stand for about 15 minutes at 20 to 35° C., it is washed with water of 40° C. The hair is then shampooed with "Ravenus Designing Shampoo" (product of Kao, containing 10 wt. % of an anionic surfactant), washed with water, subjected to rinsing treatment, washed with water and then towel-dried. The hair is then dried naturally or by a dryer.

TABLE 6

| | Form of 1st part and 2nd part | 1st Part | 2nd Part | 3rd Part | Mixing ratio by weight |
|---|---|---|---|---|---|
| Hair dye | Cream - Cream | Any one of A to H | A | — | 1:1 |
| | | A | B | — | 1:1 |
| | | I or J | C | — | 1:1 |
| | Liquid - Liquid | L | D or E | — | 1:1 |
| | Cream - Liquid | A | G | — | 1:1 |
| | | J | E | — | 1:1 |
| | | I | F | — | 1:1 |
| Bleach | Cream - Cream | K | A | — | 1:1 |
| | Liquid - Liquid | M | E | — | 1:1.5 |
| | Cream - Liquid | K | G | — | 1:1.5 |
| | Cream - Cream | K | A | A | 1:1.5:0.5 |
| | Liquid - Liquid | M | E | A | 1:1.5:0.5 |
| | Cream - Liquid | K | G | A | 1:1.5:0.5 |

Examples of the calculation method of the reduced amino equivalent in the case of (1) first part A/second part A, (2) first part B/second part A, and (3) first part E/second part A (mixing ratio 1:1) are shown in Table 7.

TABLE 7

| | Example (1) | Example (2) | Example (3) |
|---|---|---|---|
| First part | A | B | E |
| Second part | A | A | A |
| Mixing ratio (by weight) | 1:1 | 1:1 | 1:1 |
| Total silicone concentration in 1st part (wt. %) | 6.500 | 6.900 | 6.000 |
| Mole concentration of amino, imino and ammonium groups of amino-modified silicone in 1st part (mol %) | $5.56 \times 10^{-4}$ | $7.78 \times 10^{-4}$ | $8.06 \times 10^{-4}$ |
| Total silicone concentration in 2nd part (wt. %) | 0.000 | 0.000 | 0.000 |
| Mole concentration of amino, imino and ammonium groups of amino-modified silicone in 2nd part (mol %) | 0.000 | 0.000 | 0.000 |
| Total weight of all the silicones in 1 g of the whole composition (g/g) | 0.033 | 0.035 | 0.030 |
| Mole number of amino, imino and ammonium groups of amino-modified silicone in 1 g of the whole composition (mol/g) | $2.78 \times 10^{-6}$ | $3.89 \times 10^{-6}$ | $4.03 \times 10^{-6}$ |
| Reduced amino equivalent (g/mol) | 11700 | 8871 | 7448 |

The invention claimed is:

1. A hair dye composition, which comprises an amino-modified silicone, a highly polymerized silicone having a number-average degree of polymerization of 1000 or greater wherein said highly polymerized silicone is at least one selected from the group consisting of methylpolysiloxane, methylphenylpolysiloxane and hydroxyl terminal dimethylpolysiloxane, a cationic polymer, an oxidizing agent and an alkali agent.

2. The hair dye composition according to claim 1, which comprises the amino-modified silicone, highly polymerized silicone having a number-average degree of polymerization of 1000 or greater and further other silicones which are not amino-modified silicones and highly polymerized silicones in a ratio that the reduced amino equivalent expressed by the following equation:

Reduced amino equivalent (g/mol)={total weight of all the silicones in 1 g of the whole composition (g/g)}/{total moles of amino, imino and ammonium groups of the amino-modified silicone in 1 g of the whole composition (mol/g)} falls within a range of from 500 to 100000 g/mol.

3. The hair dye composition according to claim 1, further comprising a higher alcohol.

4. The hair dye composition according to claim 1, further comprising a surfactant.

5. The hair dye composition according to claim 1, wherein the alkali agent is ammonia or monoethanolamine.

6. The hair dye composition according to claim 5, further comprising a carbonate salt as the alkali agent.

7. The hair dye composition according to claim 1, which has a pH of from 7.5 to 12.

8. The hair dye composition according to claim 1, wherein said amino-modified silicone is represented by formula (1):

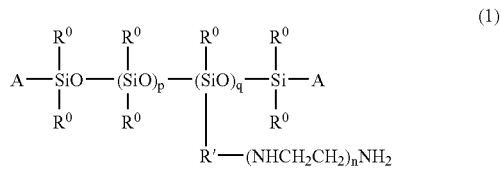

wherein, $R^0$ represents a hydroxyl group, a hydrogen atom or R, R represents a substituted or unsubstituted monovalent hydrocarbon group having from 1 to 20 carbon atoms, A represents R, a group $-R'-(NHCH_2CH_2)_nNH_2$, a group OR or a hydroxyl group, R' represents a divalent hydrocarbon group having from 1 to 8 carbon atoms, n stands for 0 to 3, and p and q are numbers, the sum of which is, in number average, 10 or greater but less than 1000.

9. The hair dye composition according to claim 1, wherein a content of said amino-modified silicone in said composition is from 0.01 to 30 wt. %.

10. The hair dye composition according to claim 1, wherein a total content of said amino-modified silicone, said highly polymerized silicone and further other silicones in said composition is from 0.02 to 40 wt. %.

11. The hair dye composition according to claim 1, wherein said cationic polymer is at least one selected from the group consisting of cationic cellulose derivatives, cationic starches, cationic guar gum derivatives, polymers or copolymers of a diallyl quaternary ammonium salt and quaternized polyvinylpyrrolidone derivatives.

12. The hair dye composition according to claim 11, wherein said cationic polymer is a polymer or copolymer of a diallyl quaternary ammonium salt and is at least one selected from the group consisting of a dimethyldiallylammonium chloride polymer, dimethyldiallylammonium chloride/acrylic acid copolymer, and dimethyldiallylammonium chloride/acrylic copolymer.

13. The hair dye composition according to claim 1, wherein a content of said cationic polymer in said composition is from 0.001 to 20 wt. %.

* * * * *